Figure 1:
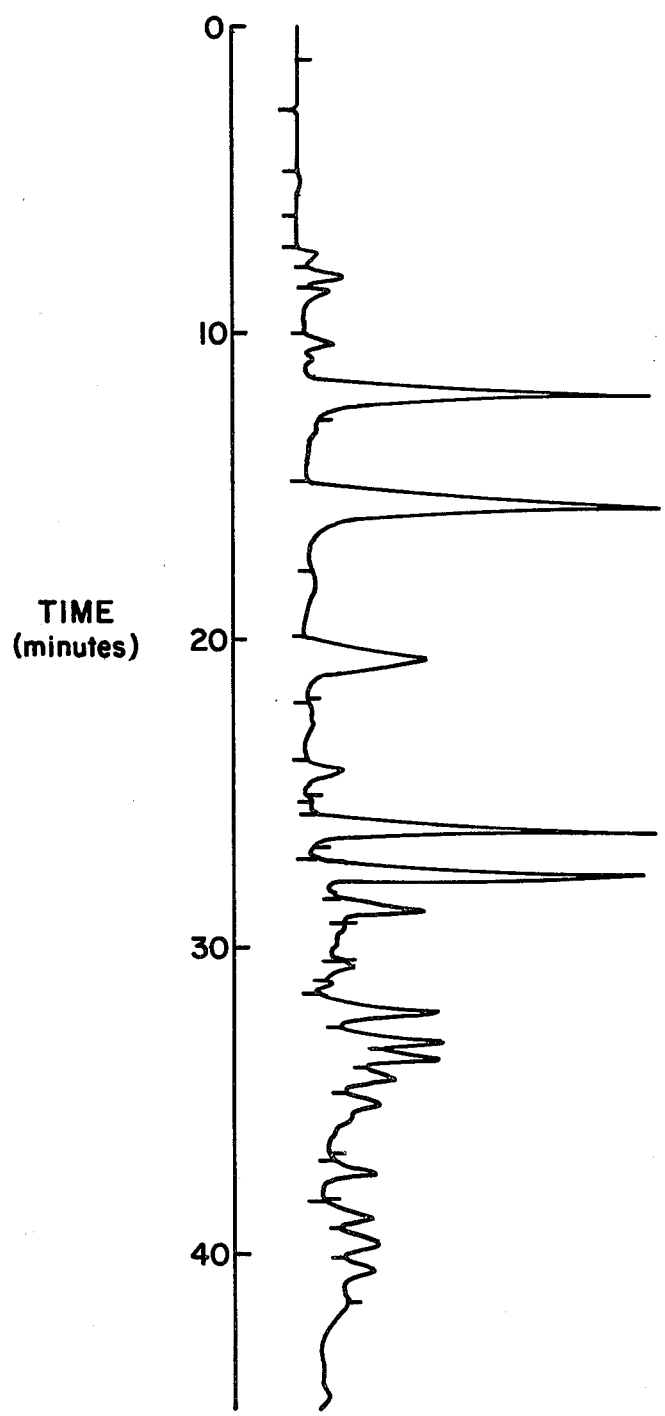

United States Patent [19]

Santer et al.

[11] 4,433,143

[45] Feb. 21, 1984

[54] METHYLATED METHYLOLATED MELAMINE COMPOSITION

[75] Inventors: J. Owen Santer, East Longmeadow; George T. Spitz, Longmeadow, both of Mass.

[73] Assignee: Monsanto Company, St. Louis, Mo.

[21] Appl. No.: 300,549

[22] Filed: Sep. 9, 1981

[51] Int. Cl.³ .......................................... C07D 251/70
[52] U.S. Cl. .................................................... 544/196
[58] Field of Search ........................................ 544/196

[56] References Cited

U.S. PATENT DOCUMENTS

| | | | |
|---|---|---|---|
| 2,763,649 | 9/1956 | Albrecht et al. | 544/196 |
| 3,824,232 | 7/1974 | Pusch et al. | 544/196 |
| 4,101,520 | 7/1978 | Boldizar | 528/248 |
| 4,271,286 | 6/1981 | Michel et al. | 528/254 |

*Primary Examiner*—John M. Ford
*Attorney, Agent, or Firm*—R. Bruce Blance; William J. Farrington; Paul D. Matukaitis

[57] ABSTRACT

A partially methylated partially methylolated melamine composition comprising a fraction of highly polar monomers characterized by liquid chromatography elution ratios. The composition is useful as a crosslinking agent for coating resins and provides curable coating systems capable of fast cure response at relatively low curing temperatures.

4 Claims, 2 Drawing Figures

FIGURE I

METHYLATED METHYLOLATED MELAMINE COMPOSITION

This invention relates to methylated methylolated melamine compositions and in particular to polar methylated methylolated melamine compositions containing a fraction of polar monomers, and to the use of such compositions as crosslinking agents in mixture with other polyfunctional materials.

Alkylated methylolated triazine compositions have been known for many years. The products range from simple compounds such as the partially and fully methylated, partially and fully methylolated triazines which are monomeric but which are capable of being converted into resinous materials and can be used with polymeric materials as crosslinking agents, to oligomeric and polymeric materials which are in fact the polymers of the simple compounds. Commercially available alkylated methylolated triazine compositions are used as crosslinking agents for polymeric materials in surface coating compositions. Especially useful in surface coating compositions are the substantially fully methylated substantially fully methylolated melamines such as hexamethoxymethylmelamine and the oligomers thereof. While such melamine derivatives give excellent cured coatings, they suffer from disadvantages in that they require high curing temperatures and they generate substantial amounts of volatile products such as formaldehyde and methanol in the crosslinking reaction. Partially methylated partially methylolated melamines in the prior art contain a high oligomer content and a high methylol content and when they are formulated with conventional coating resins to provide curable coating compositions, the compositions tend to exhibit poor compatibility, generate excessive amounts of formaldehyde upon cure, are deficient in stability and provide coatings which lack humidity resistance. More recently partially methylated partially methylolated melamine compositions with a relatively high degree of methylolation have been developed.

We have now discovered partially methylated partially methylolated melamines which can be formulated with conventional coating resins to provide stable coating compositions capable of cure at relatively low temperatures. The melamines have a moderate degree of methylolation, a substantial monomeric fraction of about 30 weight percent or more and an oligomer content of not more than about 70 weight percent. The partially methylated, partially methylolated melamines are characterized by liquid chromatography carried out under conditions set forth hereinbelow and have a first liquid chromatographic elution ratio in the range of about 0.1 to about 1.5 and a second chromatographic elution ratio in the range of about 0.2 to about 1.1. Advantageously the combined formaldehyde content of the melamine compositions is in the range of about 2.0 to about 3.3 moles per mole of melamine, and the combined methanol content is in the range of about 2.0 to about 3.0 moles per mole of melamine and about 0.7 to about 1.0 mole per mole of combined formaldehyde. More preferably the combined formaldehyde content is in the range of about 2.4 to about 3.2 and the combined methanol content is in the range of about 2.3 to about 3.0 moles per mole of melamine.

The partially methylated partially methylolated melamine composition of the present invention is prepared by reaction of melamine and formaldehyde or formaldehyde generating compounds such as paraformaldehyde under alkaline conditions to form the methylolmelamine, followed by reaction of the methanol with the methylolmelamine under acid conditions.

To obtain the desired ratio of combined formaldehyde at the methylolation step, formaldehyde and melamine are mixed in a mole ratio of about 3.0 to about 5.0. Methanol may be included in the reaction medium especially when either paraformaldehyde or concentrated aqueous formaldehyde is used as the source of formaldehyde. The pH for the methylolation step is adjusted to a point in the range of about 8.0 to about 9.0 by addition of base and the reaction is carried out at a temperature in the range of about 50° C. to reflux temperature. Preferably the methylolation step is carried out in the minimum time necessary to achieve the desired degree of methylolation. At reflux, this time is usually in the range of about 10–20 minutes. The reaction product is then cooled to about 50° C. while methanol is added to provide a mole ratio of methanol to initial melamine of at least about 8, and a weight ratio of methanol to water of at least about 2:1 and more preferably at least about 3:1. The pH is adjusted to below about 5.0 and the reaction mass is heated at a temperature in the range of about 50° to about 60° C. until the desired degree of methylation has been obtained. Preferably the methylation reaction is carried out in two steps with water, methanol and much of the uncombined formaldehyde being stripped off between the first and second steps by distillation at atmospheric pressure or preferably under reduced pressure. Prior to distillation, the pH is adjusted with base to above about 8.0 so that oligomerization is minimized during the distillation. In the second methylation step, at least about 5 more moles of methanol per initial mole of melamine are added, and the pH is readjusted to below about 5.0 and methylation is continued at a temperature in the range of about 50° to about 60° C. until the desired degree of methylation is obtained. Once more the product is adjusted to a pH above about 8, and excess methanol, water and any residual formaldehyde are distilled. The final syrup may be diluted with an appropriate solvent to adjust the viscosity.

The amount of acid added to adjust the pH and catalyze the methylation steps is preferably limited to the minimum which will provide a reasonable rate of methylation. Preferably the amount added at each step is less than about 0.02 mole per mole of melamine.

The conditions of reaction, in particular the temperatures and reaction times are limited to ensure that the oligomer fraction is not more than 70 weight percent and they can be readily limited to provide a product within the preferred degrees of methylation and methylolation, containing no more than about 60 weight percent of oligomer. The term oligomer is applied to those molecules of partially methylated partially methylolated melamine which contain two or more melamine moieties formed by condensation of methylol or methoxymethyl groups. The oligomer fraction is determined by gel phase chromatography.

Since the degree of methylolation of the melamine compositions of the present invention is low, a substantial —NH content remains contributing to the polarity of the compositions and making them highly reactive in crosslinking reactions with surprisingly no adverse effect on the stability of coating compositions containing the crosslinkers. When a liquid chromatogram of the compositions is obtained by means of a Beckman 421

Chromatography Instrument, the large concentrations of the polar components are revealed. Indeed the compositions of the present invention are characterized from liquid chromatographic elution ratios determined from the liquid chromatograph obtained when the Beckman instrument equipped with Model 100A pumps is operated at 25° C. with a column of 0.15 m in length and 4.6 mm internal diameter packed with a packing of fine silica of 5 micron average particle size comprising, an octadecylsilane surface as the stationary phase, the packing being available from Altex Scientific Inc. under the tradename Altex Ultrasphere ODS. The analytical samples contain 0.25 weight percent of the melamine composition in a solvent comprising 33 weight percent methanol and 67 weight percent water, the sample loop size being 5 microliters. The mobile phase composition injected at a rate of 0.4 ml per minute, comprises 33 weight percent methanol and 67 weight percent water during the first 10 minutes of the chromatographic analysis and 33 weight percent of ethanol and 67 weight percent of water during the remaining time. The detector is a Hitachi 100-40 Ultraviolet Detector set at 245 nm. The recorder is set to provide a chart speed of 5 mm per minute with the ordinate set at 0.1 absorbance units full scale. The first elution ratio is the sum of the areas of peaks preceding the peak which appears at about 11.7 minutes from the start of the analysis divided by the sum of the areas of peaks in the range including the peak appearing at about 11.7 minutes up to and including the peak appearing at about 15.3 minutes. The second elution ratio is the sum of the areas of peaks in the range beginning after the peak appearing at about 15.3 minutes up to and including the peak appearing at about 27 minutes divided by the sum of the areas of the peaks in the range including the peak appearing at about 11.7 minutes up to and including the peak appearing at about 15.3 minutes. Chromatograms are reproduced in FIGS. 1 and 2. In general, the reactive melamine compositions of the present invention are characterized by a first elution ratio in the range of about 0.1 to about 1.5 and a second elution ratio in the range of about 0.2 to about 1.1. More preferably for a balance in reactivity, solvent and water tolerance and crosslinking performance, the melamine compositions contain a combined formaldehyde content in the range of about 2.4 to about 3.2 and a combined methanol content in the range of about 2.3 to about 3.0 and yield chromatograms with first and second elution ratios in the range of about 0.1 to about 0.4 and about 0.3 to about 1.0 respectively.

The elution ratios characterize the monomeric components. The oligomeric fraction can be eluted from the column with a solvent comprising ethanol and methanol in a 5:95 weight ratio. In general the conditions of methylation which are selected to provide the desired polar monomer fraction characterized by the elution ratios set forth hereinabove, are also effective in limiting the oligomer content and in producing a melamine composition of low molecular weight. The molecular weight determined by vapor phase osmometry in methyl ethyl ketone is generally in the range of about 250 to about 500 corresponding to a degree of polymerization in the range of about 1 to about 2.

The partially methylated partially methylolated melamine compositions of the present invention are useful as crosslinking agents especially for surface coating compositions and can be combined with a broad class of polyfunctional compounds containing reactive groups selected from the group consisting of alcoholic hydroxy groups, carboxy groups, primary and secondary amide groups and urethane groups. The amount of these groups may be varied in the range of about 2 to about 20 weight percent based on the weight of the polyfunctional compound. The amount of methoxymethylmelamine composition used with such reactive compounds can be varied in the range of about 5 to about 60 parts by weight with correspondingly from about 95 to about 40 parts by weight of polyfunctional compound. Preferably the polyfunctional compound has a number average molecular weight of at least about 300 and preferably in the range of about 500 to about 10,000.

The polyfunctional compound may be a vinyl addition polymer formed by interpolymerization of acid, hydroxy, or amide monomer and non-functional vinyl monomers such as acrylic monomers, styrene monomers, vinyl esters and acrylonitriles and the like. The acid monomer may be selected from the group consisting of acrylic acid, methacrylic acid, crotonic acid, maleic acid, fumaric acid, itaconic acid and the monohydrocarbyl esters of monounsaturated polyacids such as the alkyl hydrogen maleates and alkyl hydrogen fumarates for example methyl hydrogen maleate, butyl hydrogen maleate, octyl hydrogen fumarate and the like. The hydroxy monomer may be selected from the group consisting of hydroxyhydrocarbyl esters of monounsaturated mono- and poly-acids such as 2-hydroxyethyl acrylate, 2-hydroxyethyl methacrylate, 2-hydroxypropyl acrylate, 3-hydroxypropyl methacrylate, bis(2-hydroxyethyl) maleate, bis(3-hydroxypropyl) fumarate and the like. The amide monomer may be selected from the group consisting of acrylamide, methacrylamide, and N-hydrocarbylacrylamides such as N-methylacrylamide and N-ethylacrylamide and the like. Also the polyfunctional compound can be selected from conventional polyester, polyamide, polyether-urethane and polyesterurethane condensation products. The polyester condensation products include conventional oil-free and oil modified alkyd resins and oil-free and oil modified urethanealkyds. In general the condensation polymers possess a functionality of at least two provided by carboxy, and/or hydroxy, and/or primary or secondary amide and or urethane groups. The polyfunctional compound can also be a polyhydric alcohol such as a styrene-allyl alcohol copolymer or a polyether polyol.

The surface coating compositions comprising polyfunctional compound and the methylated methylolated melamine composition may also include solvents to provide a viscosity suitable for the method of application. They may also include various conventional modifiers such as catalysts, accelerators, flow control agents, surface active agents, heat-stable organic and inorganic pigments, inert fillers, inhibitors and plasticizers.

The methylated methylolated melamines of the present invention are particularly suitable for use in water-reducible systems and in high solids organic solvent systems. They allow stable coating systems to be obtained, capable of fast cure at low temperature without catalyst to provide cured coatings which have excellent water resistance and durability to UV exposure. The systems show improved wetting of oily steel and reduced cratering.

EXAMPLES OF THE INVENTION

The following examples illustrate the invention. Parts and percentages are by weight unless otherwise indicated.

EXAMPLE 1

An aqueous methanolic solution of formaldehyde containing 147 parts by weight of formaldehyde, 63 parts by weight of methanol and 80 parts by weight of water, in a reaction vessel equipped with a stirrer, reflux condenser, condensate receiver and thermometer, is adjusted to a pH of 8.2 with dilute aqueous sodium hydroxide solution and 126 parts by weight of melamine are added. The resulting slurry is heated to 71° C. over about 10 minutes, and maintained between 71° to 75° C. for an additional 10 minutes to effect reaction between formaldehyde and melamine.

Following the methylolation reaction, 277 parts of methanol are added. 1.9 parts of 35% nitric acid are added as catalyst for the first methylation reaction which is conducted at about 57° C. for forty five minutes. The methylation is terminated by adjusting the pH to approximately 10.2 with aqueous sodium hydroxide.

The resulting syrup is concentrated by distillation to a terminal temperature of 80° C. at a pressure of 0.1 atmospheres at which point, an additional 332 parts of methanol is added. 1.2 parts of 35% nitric acid is added as catalyst for the second methylation reaction which is conducted at a temperature of about 55° C. for 30 minutes. The reaction is terminated by adjusting the pH to about 10.2 with aqueous sodium hydroxide.

The batch is concentrated to a terminal temperature of 110° C. at a pressure of 0.1 atmospheres, and distilled under these conditions for an additional 20 minutes to effect near complete removal of volatiles. The resulting resin is diluted, with n-butanol to provide a solids content of 85.7% and filtered to remove by-product salts.

The filtered syrup has a Gardner Holdt viscosity between $Z_1$ and $Z_2$, and a solvent tolerance of 10.0.

In addition, analysis by nuclear magnetic resonance shows that 3.2 moles of formaldehyde, and 2.8 moles of methanol are combined per mole of melamine.

Analysis of molecular size by gel permeation chromatography shows that this resin is approximately 55% oligomeric, and 45% monomeric. The number average molecular weight is about 470.

The liquid chromatogram of the resin is presented in FIG. 1. The first elution ratio as defined hereinabove, is 0.104 and the second elution ratio is 0.918.

Carbon 13 Nuclear Magnetic Resonance Spectra are obtained on a Jeol FX90Q $C^{13}$ NMR Spectrometer operating at 22.5 MegaHz., in gated mode. The carbon pulse width is 19 microsec (90°) with at least 30 sec. between pulses. Pulses are accumulated over at least 6 hours. Samples for NMR analysis are 50 percent solutions of the methylated methylolated melamine in acetone or dimethyl sulfoxide. The triazine ring carbon concentration is determined from the peak at the chemical shift between 166 and 167.5 ppm, the combined formaldehyde from the peaks at 64.5 to 72.6 ppm and the methyl of the $CH_3OCH_2$ group from the peaks at 53.9 to 55.4 ppm.

Gel permeation chromatography is carried out with a Waters Associates GPC model 200 instrument. The column comprises five sections each 1.22 m. long by 0.953 cm diameter, connected in series. Nominal pore size of Styrogel packing in each column is $10^4$ Å, 3000 Å, 250 Å, 60 Å, 60 Å respectively. Tetrahydrofuran is used as solvent at a flow rate of 1.0 ml. per minute; temperature is controlled at 45° C. Sample concentration is approximately 2 mg/ml, and 2.0 ml. are injected. The column is calibrated with commercially available, narrow distribution, polystyrene, and polypropylene glycol standards.

In the determination of solvent tolerance, 10±0.1 grams of resin solution is dissolved into 10.0 ml. of a 3/1 by weight mixture of toluene and n-butanol, in a standard 4-ounce glass jar. The resulting solution is titrated at 25°±1° C. with a hydrocarbon solution containing 84.0% isooctane, 8.0% decalin, and 8.0% toluene by weight until precipitation of resin causes 10 point print to become illegible when viewed vertically through the titrated mixture. The solvent tolerance is reported as the milliliters of hydrocarbon solution titrated per 10 grams. of resin solution sample.

EXAMPLE 2

Example 2 is prepared by the process of Example 1. The initial aqueous methanolic solution of formaldehyde, contains 129 parts by weight of formaldehyde, 63 parts by weight of methanol and 66 parts by weight of water. The first and second methanol charges for the methylation step are 475 and 554 parts by weight respectively. The resin is diluted with n-butanol to provide a solids content of 79.2 percent. The Gardner viscosity is Y and the solvent tolerance is 7. The average composition of the methylated, methylolated melamine product M/F/Me, is about 1/2.4/2.3. The monomer content by gel phase chromatography is about 65 percent. The number average molecular weight is about 380.

Figure 2:
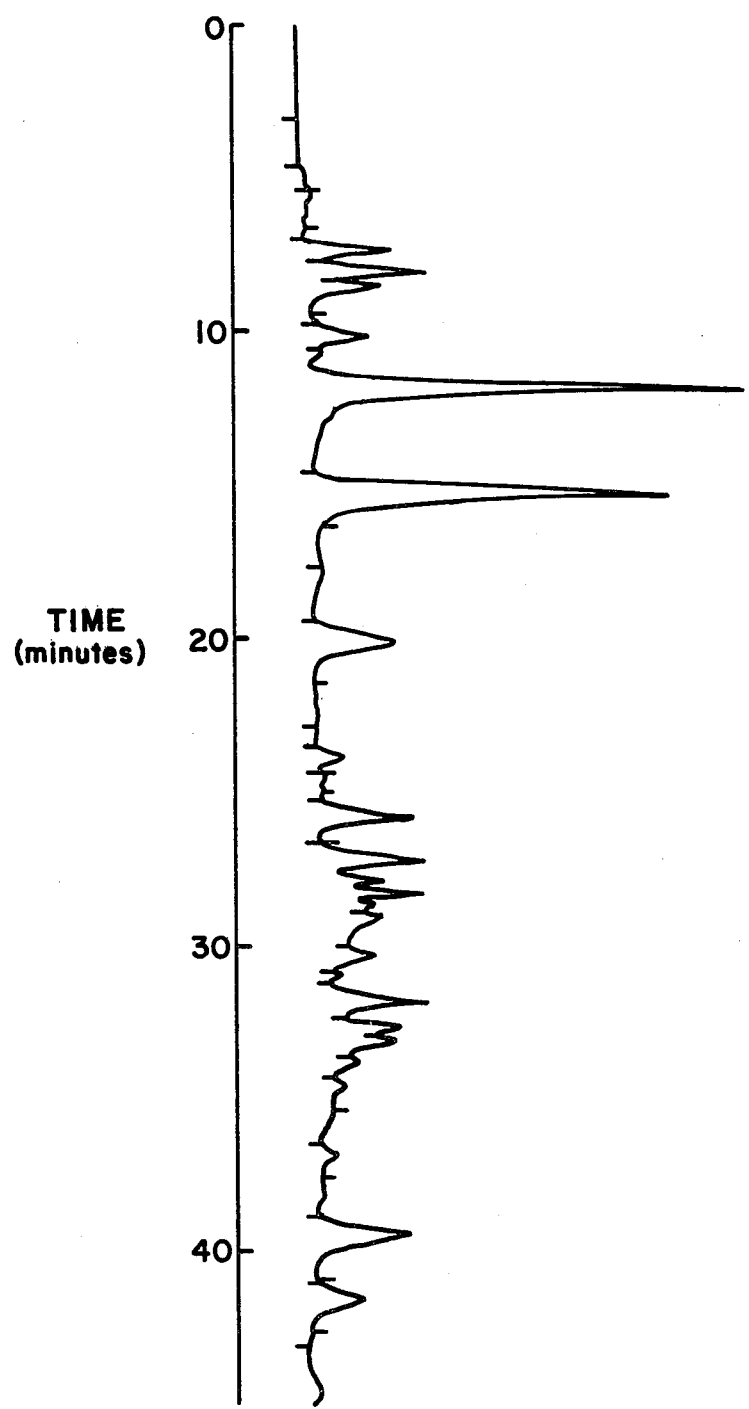

The liquid chromatogram of the methylated methylolated melamine is presented in FIG. 2. The first and second elution ratios are 0.30 and 0.37 respectively.

EXAMPLE 3

Example 3 is prepared by the process of Example 1. The initial aqueous methanolic solution of formaldehyde, contains 104 parts by weight of formaldehyde, 63 parts by weight of methanol and 52 parts by weight of water. The first and second methanol charges for the methylation step are 475 and 238 parts by weight respectively. The product contains 78.1 percent solids and has a solvent tolerance of 0.8. The average composition of the methylated methylolated melamine product M/Fe/Me, is 1/1.9/1.6. The monomer content is 74 weight percent, and the number average molecular weight is about 350. The first and second chromatographic elution ratios are 1.79 and 0.81 respectively.

COMPARATIVE EXAMPLE 4

Comparative example 4 is a commercially available methylated methylolated melamine crosslinking agent containing 81 percent solids, having solvent tolerance of 12.5. The average composition M/F/Me of the methylated methylolated melamine is 1/3.6/3.1, the oligomer content is 50 percent by weight, the number average molecular weight is 450, and the first and second chromatographic elution ratios are 0.04 and 1.33 respectively.

EXAMPLE 5

A commercially available water dilutable hydroxy acrylic resin sold by the Spencer-Kellogg Division of Textron Inc. under the tradename Arolon 557-B-70 is blended separately with the melamine crosslinking agents of Examples 1-4 at various blend ratios. Titanium dioxide pigment is dispersed in the blends to provide a pigment to binder ratio of 0.8 and a total solids of 35 percent. The pigmented coating compositions are coated on test panels, dried and baked for 10 minutes at 121° C. to give films of about 20 microns in thickness. The cured coatings are tested for hardness and humidity resistance. The data are presented in Table 1. The data show that the methylated methylolated melamine of example 3 is quite deficient as a crosslinker since even at a 60/40 ratio of resin to crosslinker, the cured coating possesses a rather modest Tukon hardness. Also it exhibits incompatibility with acrylic and polyester resins. The data further show that examples 1 and 2 within the scope of the invention, give coatings with superior hardness, condensing humidity resistance and QUV resistance especially at high ratios of crosslinker to resin, in comparison with coatings prepared with the crosslinker of comparative example 4.

blended separately with the melamine crosslinking agents of Examples 1 and 4 at a 70/30 resin-crosslinker weight ratio. Titanium dioxide is dispersed in the blends to provide a pigment to binder ratio of 0.8 and a total solids of 51 weight percent. The pigmented coating compositions are coated on test panels, dried and baked for 20 minutes at 121° C. to give films of about 23 microns in thickness. The cured coatings are tested for hardness, solvent resistance, gloss humidity and corrosion resistance. The data are presented in Table 3 and again demonstrate the superiority in hardness, solvent resistance and humidity resistance of the crosslinkers of the present invention imparted by the low degree of methylolation and the high concentration of polar components.

TABLE 1

COATINGS PREPARED FROM AROLON 557-B-40 HYDROXY FUNCTIONAL ACRYLIC RESIN

|  | Example 1 | | | Example 2 | | | Example 3 | Example 4 | | |
| --- | --- | --- | --- | --- | --- | --- | --- | --- | --- | --- |
| Resin/crosslinker ratio | 80/20 | 70/30 | 60/40 | 80/20 | 70/30 | 60/40 | 60/40 | 80/20 | 70/30 | 60/40 |
| Cure volatiles, % | 18 | 14 | 12 | 13 | 11 | 10 | — | 17 | 14 | 13 |
| Tukon hardness | 16.2 | 17.1 | 18.0 | 16.1 | 17.6 | 18.6 | 1.4 | 15.7 | 15.7 | 16.1 |
| Condensing Humidity, 66° | | | | | | | | | | |
| Initial gloss, 20°/60° | 87/93 | 90/94 | 91/94 | 89/93 | 92/94 | 92/95 | — | 88/93 | 89/94 | 91/94 |
| Gloss after 18 hours | 1/6 | 14/42 | 86/93 | 1/7 | 60/81 | 85/92 | — | 1/5 | 1/5 | 4/30 |
| Gloss after QUV exposure: | | | | | | | | | | |
| 24 hours | 76/94 | 76/94 | 66/84 | 54/86 | 76/92 | 74/91 | — | 62/92 | 30/69 | 29/68 |
| 100 hours | 6/28 | 30/71 | 38/34 | 2/11 | 22/47 | 66/89 | — | 4/22 | 1/5 | 1/5 |
| Gloss after immersion in boiling water (1 hr.) | 37/79 | 3/20 | 45/73 | 14/54 | 1/5 | 2/16 | 7/40 | 30/73 | 9/35 | 1/5 |

EXAMPLE 6

A commercially available oil-free hydroxy functional polyester resin sold by Cargill Co. under the tradename Polyester XP-5770-85 as an 85 percent solution in Cellosolve acetate, with acid number 8.5 max, hydroxyl number 152±4 and equivalent weight 370±10, is blended separately with the melamine crosslinking agents of Examples 1 and 4 at a 70/30 resin/crosslinker weight ratio. Titanium dioxide is dispersed in the blends to provide a pigment to binder ratio of 0.8 and a total solids of 83 percent by weight. The pigmented coating compositions are coated on test panels, dried and baked for 20 minutes at 121° C. to give films of about 33 microns in thickness. The cured coatings are tested for hardness, solvent resistance, gloss, and humidity and corrosion resistance. The data are presented in Table 2 and again demonstrate the superiority of the crosslinkers of the present invention imparted by the low degree of methylolation and the high concentration of polar components.

TABLE 2

COATINGS PREPARED FROM CARGILL XP-5770-85/POLYESTER RESIN

|  | Ex. 1 | Comparative Example 4 |
| --- | --- | --- |
| Tukon Hardness | 4.1 | 1.9 |
| 20° Gloss | 88 | 73 |
| MEK Rubs | 25 | 18 |
| Condensing Humidity - 500 hrs. 20° Gloss | 35 | 2 |
| Salt Fog - 64 hrs. | | |
| Blistering | 0 | 0 |
| Scribe Fail | ⅛" | ⅛" |

EXAMPLE 7

A commercially available water soluble acrylic resin sold by Rohm and Haas under the tradename WS78 is

TABLE 3

COATINGS PREPARED FROM WS78/AQUEOUS ACRYLIC RESIN

|  | Ex. 1 | Comparative Example 4 |
| --- | --- | --- |
| Tukon Hardness | 17.6 | 14.9 |
| 20° Gloss | 77 | 81 |
| MEK Rubs | 112 | 91 |
| Condensing Humidity - 72 hrs. 20° Gloss | 5 | 2 |
| Salt fog exposure - 64 hrs. | | |
| Blistering | 9.5–75% | 9.5–10% |
| Scribe Failure % | 80 | 20 |

EXAMPLE 8

A commercially available hydroxy functional acrylic resin solid by Rohm and Haas under the tradename Acryloid AT-410 as a 73 percent solution in methyl n-amyl ketone, with a hydroxyl number of 64 and an acid number of 28, is blended separately with the melamine crosslinking agents of Examples 1 and 4 at a 70/30 resin/crosslinker weight ratio. Titanium dioxide is dispersed in the blends to provide a pigment to binder ratio of 0.8 and a total solids of 70 weight percent. The pigmented coating compositions are coated on test panels, dried and baked for 20 minutes at 116° C. The cured coatings are tested for hardness, solvent resistance, gloss, and humidity and corrosion resistance. The data are presented in Table 8 and again demonstrate the superiority of the crosslinkers of the present invention imparted by the low degree of methylolation and the high concentration of polar components.

TABLE 4

COATINGS PREPARED FROM ACRYLOID AT-410

|  | Ex. 1 | Comparative Example 4 |
| --- | --- | --- |
| Tukon Hardness | 18.6 | 16.6 |

TABLE 4-continued

COATINGS PREPARED FROM ACRYLOID AT-410

|  | Ex. 1 | Comparative Example 4 |
| --- | --- | --- |
| 20° Gloss | 92 | 82 |
| MEK Rubs | 58 | 32 |
| Condensing Humidity 500 hrs. 20° Gloss | 75 | 36 |
| Salt Fog - 64 hrs. | | |
| Blistering | 0 | 0 |
| Scribe Fail | 1/8" | 1/8" |

EXAMPLE 9

A commercially available hydroxy functional acrylic emulsion sold by Rohm and Haas Co. under the tradename Rhoplex AC-1533 is blended separately with the melamine crosslinking agents of Examples 1 and 4 at a 70/30 resin/crosslinker weight ratio. Titanium dioxide is dispersed in the blends to provide a pigment to binder ratio of 0.8 and a total solids of 58 weight percent. The pigmented coating compositions are coated on test panels, dried and baked for 20 minutes at 116° C. to give films of about 28 microns in thickness. The cured coatings are tested for hardness, solvent resistance, gloss, and humidity and corrosion resistance. The data are presented in Table 5 and again demonstrate the superiority of the crosslinkers of the present invention imparted by the low degree of methylolation and the high concentration of polar components.

TABLE 5

COATINGS PREPARED FROM RHOPLEX AC-1533/ACRYLIC EMULSION

|  | Ex. 1 | Comparative Example 4 |
| --- | --- | --- |
| Tukon Hardness | 7.1 | 3.8 |
| 20° Gloss | 78 | 74 |
| MEK Rubs | 200 | 35 |
| Condensing Humidity - 500 hrs. 20° Gloss | 70 | 42 |
| Salt Fog - 124 hrs. | | |
| Blistering | 0 | 0 |
| Scribe Fail | 1/16" (25%) | Negl. |

What is claimed is:

1. A methylated methylolated melamine composition comprising a combined formaldehyde content in the range of about 2.4 to about 3.2 moles per mole of melamine and a combined methanol content in the range of about 2.3 to about 3.0 moles per mole of melamine and a combined methanol content in the range of about 0.7 to about 1.0 mole per mole of combined formaldehyde and possessing a first elution ratio in the range of about 0.1 to about 1.5 and a second elution ratio in the range of about 0.2 to about 1.1, and an oligomer content of no more than about 70 percent by weight.

2. The melamine composition according to claim 1 wherein the first liquid chromatographic elution ratio is in the range of about 0.1 to about 0.4 and the second liquid chromatographic elution ratio is in the range of about 0.3 to about 1.0.

3. The melamine compositions of claim 2 or 1 wherein the hydrocarbon solvent tolerance is in the range of about 2 to about 10.

4. The melamine compositions of claim 2 or 1 wherein the number average molecular weight is in the range of about 250 to about 500.

* * * * *